(12) United States Patent
Jolliffe et al.

(10) Patent No.: US 11,737,404 B2
(45) Date of Patent: Aug. 29, 2023

(54) HYBRID CEREAL SEED PRODUCTION

(71) Applicant: LIMAGRAIN EUROPE, Saint-Beauzire (FR)

(72) Inventors: Thomas Jolliffe, Lincoln (GB); Mark Glew, Lincolnshire (GB); Mark Rusling, Lincolnshire (GB); Alain Murigneux, La Roche Blanche (FR); Pierrick Varenne, Chartres (FR)

(73) Assignee: LIMAGRAIN EUROPE, Saint-Beauzire (FR)

( * ) Notice: Subject to any disclaimer, the term of this patent is extended or adjusted under 35 U.S.C. 154(b) by 0 days.

(21) Appl. No.: 15/125,007

(22) PCT Filed: Mar. 10, 2015

(86) PCT No.: PCT/EP2015/054963
§ 371 (c)(1),
(2) Date: Sep. 9, 2016

(87) PCT Pub. No.: WO2015/135940
PCT Pub. Date: Sep. 17, 2015

(65) Prior Publication Data
US 2017/0079224 A1 Mar. 23, 2017

(30) Foreign Application Priority Data
Mar. 10, 2014 (EP) .................................. 14305344

(51) Int. Cl.
*A01H 1/02* (2006.01)
*A01H 4/00* (2006.01)
*A01H 1/04* (2006.01)

(52) U.S. Cl.
CPC ................. *A01H 1/02* (2013.01); *A01H 1/04* (2013.01); *A01H 4/00* (2013.01)

(58) Field of Classification Search
None
See application file for complete search history.

(56) References Cited

U.S. PATENT DOCUMENTS

| 4,208,835 A | 6/1980 | Habstritt et al. |
| 4,332,107 A | 6/1982 | Reed |
| 4,464,862 A * | 8/1984 | Peterson ............. A01M 21/043 47/1.5 |
| 4,485,588 A | 12/1984 | Reed |
| 5,875,587 A | 3/1999 | Stevens |
| 2013/0167496 A1 | 7/2013 | Bensley-Bromilow et al. |
| 2017/0079224 A1 | 3/2017 | Jolliffe et al. |

FOREIGN PATENT DOCUMENTS

| AU | 2006203431 | 2/2007 |
| AU | 2006203431 A1 * | 2/2007 |
| CA | 2313068 | 12/2001 |
| CN | 1353924 | 6/2002 |
| CN | 1442038 A | 9/2003 |
| CN | 1943319 | 4/2007 |
| CN | 1943319 A | 4/2007 |
| CN | 102948361 A | 3/2013 |
| EP | 0058612 | 8/1982 |
| GB | 2305590 | 4/1997 |
| WO | WO-8300601 | 3/1983 |
| WO | WO-02053708 | 7/2002 |
| WO | WO 2012/038350 A1 * | 3/2012 |

OTHER PUBLICATIONS

Whitford et al., 2013, Journal of Experimental Botany 64: 5411-5428.*
Kempe and Gils, 2011, Molecular Breeding 27: 417-437.*
Yang et al., 2009, Dwarf Male-Sterile Wheat: A Revolutionary Breeding Approach to wheat. Food and Agriculture Organization of the United Nations (FAO), Q.Y. Shu, ed., pp. 370-372.*
Paszkiewicz and Butzen, 2007, Corn Hybrid Response to Plant Population, Crop Insights 17(16): 1-4.*
Ajayi et al., 2006, Impact of Mechanical Damage to Hybrid Maize Seed from Harvesting and Conditioning, Seed Technology 28: 1-21.*
The University of Georgia Cooperative Extension, 2012, Bulletin 973: 1-8.*
Jacob Junior et al., 2014, Ideal seeds harvest moment of different maize hybrids, Ciência Rural, Santa Maria, v.44, n.2, p. 253-260.*

(Continued)

*Primary Examiner* — Weihua Fan
*Assistant Examiner* — Brian James Sullivan
(74) *Attorney, Agent, or Firm* — B. Aaron Schulman, Esq.; Stites & Harbison, PLLC

(57) ABSTRACT

Disclosed is a method of producing hybrid seeds, in particular hybrid cereal seeds, comprising crossing a stand of shorter female (male sterile) plants (shorter than the fertile plants) with a stand of taller male fertile plants (taller than the sterile plants). The method comprises limiting the proportion of self-fertilized male seed in the final produced seed stock. In particular, the method limits the seed development on male plants after pollination to reduce or eliminate the proportion of self-fertilized male seed in the final produced seed stock. The method limits this proportion of self-fertilized male seed in the final produced seed stock, under a threshold value, preferably under a value to be compliant with a regulatory hybridity level. Limiting the seed stock of male plant comprises passing, at least once, a tool extending above the height of the shorter female plants, but below the level of the height of the taller male fertile plants, between anthesis, preferably end of anthesis, and harvest. The tool is intended to prevent or reduce normal development of these male fertile plants standing above this height. The crossing of female and male fertile plants comprises sowing the seeds as a mix or drilling male sterile seeds and male fertile plant seeds in separate lines. Preferably, said eliminating tool has means to apply an herbicide, preferably systemic, such as glyphosate.

23 Claims, No Drawings

(56) References Cited

OTHER PUBLICATIONS

Tripti Vashisth, Chapter 19, Pollination Techniques, Plant Breeding in the 21st Century, University of Georgia, available at http://plantbreeding.coe.uga.edu/index.php?title=19._Pollination_Techniques, last modified on Aug. 9, 2013.*

International Search Report for PCT/EP2015/054963, dated May 8, 2015.

Perez-Prat E et al: "Hybrid seed production and the challenge of propagating male-sterile plants", Trends in Plant Science, Elsevier Science, Oxford, GB, vol. 7, No. 5, May 1, 2002(May 1, 2002), pp. 199-203, XP002414650, ISSN: 1360-1385, DOI: 10.1016/S1360-1385(02)02252-5 the whole document.

Whitford, R., D. Fleury, J. Reif C., M. Garcia, T. Okada, V. Korzun, and P. Langridge. "Hybrid breeding in Wheat: Technologies to Improve Hybrid Wheat Seed Production." *Journal of Experimental Botany* 64.18 (2013): 5411-428. Print.

Yang, L., Liu, B.H., Zhai, H.Q., Wang, S.H., Liu, H.W., Zhou, Y., Meng, F.H., Yang, J.P., Zhu, G., Chui, S.L., Zhang, Q.H., & Wei, Y.L. (2009). Dwarf Male-Sterile Wheat: A Revolutionary Breeding Approach to wheat. Food and Agriculture Organization of the United Nations (FAO): FAO.

Cao, W., DJ Somers, and G. Fedak. "A Molecular Marker Closely Linked to the Male Sterile Ms2 Gene in Common Wheat (*Triticum Aestivum*)." (n.d.): n. pag. Rpt. in *11th International Wheat Genetics Symposium*. Sydney: Sydney UP, 2008. 1-3. Print.

Dontsova, et al, "Studying of Laws of Inheritance of Quantitative Signs at Creation of the New Initial Material of Winter Barley", UDC 633. 162. 631. 527.

Zhongqi, et al, "Heterosis of grain weight in wheat hybrids with *Triticum timopheevi* cytoplasm", 1994, pp. 189-193, vol. 75, Euphytica.

Adugna, et al, "A comparison of cytoplasmic and chemically-induced male sterility systems for hybrid seed production in wheat (*Triticum aestium* L.)", 2004, vol. 135, pp. 297-304, Euphytica.

Yenish, et al, "Effect of Preharvest Glyphosate Application on Seed and Seedling Quality of Spring Wheat (*Triticum aestivum*)", 2000, pp. 212-217, vol. 14, Weed Technology.

Farm Machinery and Equipment-II 3(2+1), Jan. 3, 2021, pp. 1-12.

Tan, et al, "Genetics of late maturity α-amylase in a doubled haploid wheat population", 2010, vol. 61, pp. 153-161, Crop & Pasture Science.

Taillebois, et al, "Improving outcrossing rate in rice", pp. 175-180.

Tian, et al, "Development of dominant nuclear male-sterile lines with a blue seed marker in durum and common wheat", 2001, vol. 120, pp. 79-81, Plant Breeding.

Pearce, et al, "Molecular Characterization of Rht-1 Dwarfing Genes in Hexaploid Wheat", Dec. 2011, pp. 1820-1831, vol. 157, Plant Physiology.

Pickett, et al, "Hybrid Wheat Results and Problems", 1993, Advances in Plant Breeding.

Hedden, et al, "The genes of the Green Revolution", Jan. 2003, pp. 5-9, vol. 19, No. 1, TRENDS in Genetics.

Malalgoda, et al, "Effects of Pre-Harvest Glyphosate Application on Spring Wheat Quality Characteristics", 2020, pp. 1-16, vol. 10, Agriculture.

De Vries, A. Ph., "Some Aspects of Cross-Pollination in Wheat (*Triticum aestivum* L.) 1. Pollen Concentration in the Field as Influenced by Variety, Diurnal Pattern, Weather Conditions and Level as Compared to the Height of the Pollen Donor", 1972, pp. 185-203, vol. 21, Euphytica.

Shu, Q.Y., "Induced Plant Mutations in the Genomics Era", 2009, pp. 370-372.

Taillebois, et al, "Improving outcrossing rate in rice (*Oryza sativa* L.)", 1989, pp. 175-180.

Rutger, et al, "A Fourth Genetic Element to Facilitate Hybrid Cereal Production—A Recessive Tall in Rice", May 1981, pp. 373-376, vol. 21, Crop Science.

* cited by examiner

HYBRID CEREAL SEED PRODUCTION

This invention is about a method to produce hybrid seed, especially hybrid cereal seed and a new use of tools and/or chemicals, especially herbicides in this context.

BACKGROUND ART

Producing hybrid seed from cereal is a major challenge for seed companies, in particular for all types of wheat, barley and rice, but any other crops reproduced by seed including crops like triticale, oats, millet or rye could also benefit from this invention.

Hybrid wheat may be obtained by the use of a chemical agent for hybridization (CHA). Male plant and female are sowed in strips, often but not always male plants are taller than female plants to promote better pollen dispersal. A CHA is used to prevent pollen formation on female plants. The only CHA commercially used is CROISOR® 100 from SAATEN-UNION.

The same production system of sowing in strips or rows can be used with male sterile (female) plants obtained from the use of genetic traits: nuclear male sterility, or cytoplasmic male sterility combined with the use of a restorer(s) to get fertile hybrid seeds. These traits can issue from native or GMO technologies and from one or several genes.

Both of these types of system imply the use of sowing in strips or rows of male and female plants. Different proportions can be used and even if the area of male strips or rows is less that the female strips or rows, the proportion of female will typically not exceed two-thirds of the total plants. Moreover, pollen dispersal may not be optimized, and harvest has to be done in a way to prevent the pollen donor being harvested with the hybrid seed.

In barley, a hybrid production system has been described by Syngenta, with a simple blend of 95% female and 5% male seed sowed. The harvest contains sufficient hybrid seed to comply with regulations for hybrid commercialization. Moreover, sowing a higher percentage of male should improve the yield of hybrid seed but doing so will also increase the proportion of male seeds in the harvested seeds. Moreover, growing hybrid seed using this mixed stand system, where 95% of the seeds are female, as opposed to in a strip growing system where for example only two-thirds are female, should improve hybrid seed productivity per unit area.

When female and male are sown to a mixed stand, the harvest includes seeds produced on the sterile female pollinated by the male and male self-pollinated seeds. Removal of seeds from the male parent in the hybrid production can be achieved in several ways. A phenotypic marker can be used to remove all or a fraction of the male self-pollinated seeds. The use of a colour marker in the production of hybrid seed using cytoplasmic male sterility is described in U.S. Pat. No. 3,842,538. Use of a blue seed marker is described in Zong-Jun Pu et al. (2005). Studies on breeding of dominant nuclear dwarf male sterile lines with a blue seed marker in common wheat, is described in wheat information Services Number 99: 46-50. WO 2012/038350 describes the use of Near-Infra-Red to select between seeds of hybrids and homozygous seeds based on phenotypic differences. The use of a system such as these seed markers implies the introgression of the corresponding phenotypic marker gene(s) into the genetic material used.

Dwarf male-sterile wheat are described in the paper of Yang et al., (2009): A revolutionary Breeding Approach to wheat, Q. Y. Shu (ed), Induced Mutation in the Genomics Era. Food and agriculture organization of the United Nations, Rome, p 370-372, and their used in wheat recurrent selection. This method is named "dwarf male-sterile wheat technical system". In this method, mixture of dwarf male sterile plants and tall male plants to have better pollination are sown Similar approaches are given in other papers, Cao W. et al., 2008, A molecular marker closely linked to the male sterile Ms2 gene in common wheat (*Triticum aestivum*) $11^{th}$ international wheat genetic symposium proceeding p1-3, said if the Taigu male sterile gene Ms2 was cloned and linked closely to a gene for herbicide resistance, it could be used for the production of commercial hybrid wheat cultivars when a fertility restorer becomes available.

OBJECTIVES OF INVENTION

There is still a need for a process to efficiently produce hybrid seed, especially of cereals, including wheat and barley.

An objective of the invention is thus to propose a new process allowing the production of hybrid seeds in an efficient and cost-effective manner.

Another objective is to propose such a process which allows one to produce hybrid seeds being within the regulatory requirements for hybridity level, in particular those of the European certification system, which is currently set at 90% for wheat, barley, rape, triticale and rice.

Another objective is to propose such a process which allows one to produce hybrid seeds efficiently, with a good or improved yield per unit of land used.

Another objective is to propose such a process which allows one to produce hybrid seeds using an improved proportion of male seeds, specifically a proportion higher than 5% with respect to male sterile seed of the total parental seeds.

Still another objective is to propose such a process which allows one to recover less male seeds in the harvest than drilled, say to reduce proportion of male seeds in the harvest compared to what was sown.

SUMMARY OF INVENTION

The process according to the invention is based on the use of male fertile plants (producing pollen for pollination of the female (male sterile) plants) taller than the female (male sterile) which offers the possibility, after the female plants have been pollinized, to destroy on a large scale the taller fertile male plants by an easy to implement process based on mechanical and/or chemical means. Moreover, the process affects the main tiller and taller secondary tillers of the male plants that are taller than the female plants, but shorter or secondary tillers can also be affected by the chemical treatment of the male plants even if these tillers have not been directly in contact with the chemical.

The method is based on the use of a height gap between fertile male and female plants, by the selection of male plants that are taller than corresponding female plants, including for example in wheat use of one or more rht gene mutation(s), female plant being shorter than the male plant. Male and female plants can be sowed as a mixture, or drilled in close rows or lines, and, after flowering, male plants can be selectively destroyed, e.g. by the use of a weed wiper or an equivalent physical/mechanical device whether or not associated with use of a herbicide. An additional selection of seed may be performed in order to eliminate undesirable male seed in the produced seed stock. By "seed stock", it is meant in the context of the present invention, the number of seeds harvested.

The invention thus concerns a method of producing hybrid seeds, especially hybrid cereal seeds, comprising crossing a stand of shorter female (male sterile) plants (shorter than the fertile plants) with a stand of taller fertile plants (taller than the female plants). The method comprises limiting the proportion of self-fertilized male seed in the final produced seed stock. Limiting the self-fertilized male seed proportion comprises passing, at least once, a tool extending above the height of the shorter female plants, but below the level of the height of the taller male fertile plants, between anthesis, preferably end of anthesis, and harvest. The tool is intended to prevent or reduce normal development of these male fertile plants standing above this height. The tool contacts these male fertile plants standing above this height and causes preventing or reducing normal development thereof.

The invention also relates to a method of producing hybrid cereal seeds from a field containing a stand of shorter female (male sterile) pollinized plants with a stand of taller male fertile plants, the method comprising passing a tool extending above the height of the shorter female plants between anthesis, preferably end of anthesis, and harvest, which tool applies a mechanical action and/or a chemical on the taller male fertile plants, whereby development of the male fertile plants standing above this height is prevented or reduced.

The method limits this proportion of self-fertilized male seed in the final produced seed stock, under a threshold value, preferably under a value to be compliant with a regulatory hybridity level.

In particular, the method limits the seed development on male plants after pollination of the female plants to reduce or eliminate the proportion of self-fertilized male seed in the final produced seed stock. The self-fertilized male seeds that may be produced may further be eliminated or reduced at the time of harvest. In addition, a proportion of the male plants may be eliminated with the straw at the time of harvest, e.g. when using a harvester.

The invention also concerns the use of a tool, such as a weed wiper, applying a chemical, preferably a herbicide and/or the use of a chemical, e.g. herbicide, preferably a herbicide that is systemic, to prevent or reduce normal development of the taller fertile plants between anthesis, preferably end of anthesis, and harvest in a field comprising shorter female (male sterile) plants and taller fertile plants for producing hybrid seeds, especially hybrid cereal seeds, wherein the chemical, e.g. herbicide is applied, at least once, to the taller fertile plants extending above the height of the shorter female plants between anthesis and harvest. The tool is applied after pollinization.

The invention also concerns the use of a tool, such as a weed wiper, applying a chemical, preferably a herbicide and/or the use of a chemical, e.g. herbicide, preferably a herbicide that is systemic, to prevent or reduce the production of self-fertilized seeds by fertile plants between anthesis, preferably end of anthesis, and harvest in a field comprising shorter female (male sterile) plants and taller fertile plants for producing hybrid cereal seeds, especially hybrid cereal seeds, wherein the chemical, e.g. herbicide is applied, at least once, to the taller fertile plants extending above the height of the shorter female plants between anthesis and harvest. The tool is applied after pollinization.

These uses are intended to limit the proportion of self-fertilized male seed in the final produced seed stock in particular under a threshold value, preferably under a value to complain with a regulatory hybridity level.

The method concerns the production of hybrid wheat, but is not limited to the production of hybrid from two inbred parental lines, this method should also be used for the production of complex hybrids: three way hybrid, double hybrid . . .

DETAILED DESCRIPTION

Crossing of female (male sterile) and male fertile plants comprises first sowing seeds of both populations in close proximity in order to ensure a high level of cross-pollination. One of the interests of the invention is to render possible a mixed sowing or sowing in close rows or another sowing method "close to mix sowing", while allowing the limitation of undesirable seeds in the final harvest, while even increasing the ratio of fertile plants and availability of pollen at the time of crossing.

In a first embodiment, crossing of female (male sterile) and male fertile plants comprises sowing the seeds as a mixture. In this embodiment, a mixture of seeds for female (male sterile) and male fertile plants in the appropriate ratio is sown.

In a second embodiment, crossing of female (male sterile) and male fertile plants comprises drilling female (male sterile) seeds and male fertile plant seeds in separate rows or lines. Preferably, seeds of female (male sterile) and seeds of male fertile plants are drilled in parallel. As an alternative, male and female seeds are sown successively on the same or "common" row. It is also possible to sow female and male using several rows or lines of one sort, then several lines or rows of the other sort, and so on, with several being preferably maintained at a low level to ensure "close proximity", in particular comprised of 2 or more lines of the same seed sort.

Limiting the seed stock from male plants comprises passing a tool extending above the height of the shorter female plants but below the level of the height of the taller male fertile plants.

In a preferred embodiment, the tool applies or has a means of applying a chemical, preferably herbicide to the taller male plants, preferably by entering into contact with the plants extending above the height of the shorter female plants. In another embodiment, the tool cuts the taller male plants above the height of the shorter female plants. By way of example, use is made of a "weed wiper" which is a device comprising a horizontal bar or support that is moveable, preferably is motor driven or supported by a motor driven vehicle. The height at which the bar is placed is preferably adjustable in order for the user to adjust its height to the height of the plants, preferably capable of being altered while travelling through a crop. The bar or support is preferably designed to deliver a chemical, preferably a herbicide to the plants entering into contact with the bar or support. For example, the bar or device comprises a roller or brush or a rope or a sponge or a blade and/or the like and a chemical, preferably a herbicide is trickled or soaked on to it. Weed wipers useful in the invention or adaptable to the invention are described in the literature, e.g.: CA 2 313 068, GB 2 305 590, U.S. Pat. No. 4,485,588, WO 95/21524, WO 83/00601, EP 058 612, U.S. Pat. Nos. 4,332,107, 4,208,835, AU 2006203431.

An alternative could be to use a cutting tool, e.g. a reaping machine with a very high level of cutting to remove specifically the taller male plants, or for example with the use of a maize detasseler. The tool is moveable, preferably is motor driven or supported by a motor driven vehicle. The height at which the cutting tool is placed is preferably adjustable in order for the user to adjust its height to the height of the plants, preferably capable of being altered while travelling through a crop.

In an embodiment, the tool such as the weed wiper or the cutting tool is motor driven and has means to adjust automatically its height to the height of the plants while travelling through a crop. These means comprises sensors for detecting the height of the female and/or male plants and to adjust its height in function of the data recovered by the sensors.

Seeds in this invention may be sown as a mixture with 5% or more male seeds, preferably about 50%, 40%, 30%, 20%, 15%, 10% or 5%. They also may be drilled in rows or lines while respecting this proportion.

The ratio at sowing or crossing of male fertile seeds or plants versus female (male sterile) seeds or plants may vary from about 5%/about 95% to about 50%/about 50%. By the use of the precision agriculture tools, this ratio and other parameters as sowing density may by continuously adapt in the field of hybrid production to assure the best hybrid seed yield according to soil and other environment data.

The present invention may be applied in particular to cereals, in particular oats, wheat, barley, rice, spelt, triticale, millet, rye, or rape. Autogamous hybrid cereals are concerned with the invention: oat (*Avena sativa* comprising byzantine; *Avena nuda; Avena strigosa*), barley (*Hordeum vulgare*), rice (*Oryza sativa*), wheat (*Triticum aestivum*), durum wheat (*Triticum durum*), spelt (*Triticum spelta*) and triticale (*Triticosecale*). Partially autogamous plants can also be concern by this invention, for example rape (Brassisa spp.).

The tool may be used as soon as the female plants have been sufficiently pollinated or as soon as the female plants finished flowering. The tool may thus be used after the onset and preferably at the end of anthesis or post-anthesis of the male sterile plants. It may be used at any time between anthesis and harvest of the seeds. A mechanical elimination may be performed e.g. using a cutting tool and its effect is immediate, the elimination may be performed at any time between anthesis and harvest, however, it is preferable to perform it as early as possible after anthesis for the sake of optimizing development of the female (male sterile) plants in the crop. A chemical, e.g. herbicidal, treatment needs some time to affect plants, so that the time of application is determined to be efficient before harvest depending on the speed of action of the chemical, e.g. herbicide, the number of chemical, e.g. herbicide applications, the weather conditions, etc., and once again, it is preferable to perform it as early as possible after anthesis for sake of optimizing development of the male sterile plants in the crop. Generally speaking, the elimination (mechanical and/or chemical) will be preferably applied between the anthesis and up to 30, 20 or 10 days after anthesis.

The herbicide used is any herbicide or any other chemical being able to compromise or stop plant growth and the seed development of cereals by an application made or effective after the onset of anthesis or at post-anthesis and in the above conditions. Preferably the herbicide is a systemic herbicide entering the plant by contact action with the plant. Preferably this herbicide is able to kill plants at this stage of development. As an example, the herbicide is glyphosate or glufosinate, preferably it is glyphosate. The herbicide may be applied once or in several applications (at least two, e.g. 2 or 3). An adjuvant can be added to the herbicide to improve its efficiency, for example improving the contact of herbicide with the plant, and may be beneficial. Therefore, one may add a component for improving permeability and diffusion of the herbicide into the plant for the systemic action to occur more efficiently.

Others components able to destroy the taller plant could be used, for example desiccants. When the tool has been used, once or more, a further manual removal of the surviving male plants can be done.

According to a feature, limiting the proportion of seeds from self-fertilized male plants comprises further, after harvesting of the seeds, a selection of the seeds to remove self-fertilized male seeds, e.g. selection using a morphological criteria or character, such as the size or density or shape or composition and/or the some other aspect of seeds (in particular prematurely desiccated or shriveled seeds) and/or using a phenotypic character for example color. These prematurely or shriveled seeds may come from the action of the herbicide, in particular but not limited from spikes issuing from tiller that are affected by the herbicide but not totally destroyed. Secondary tillers from males should also give seeds if their maturity are enough delayed regarding the main tiller but these seeds should be immature at harvest: smaller and/or greener. This elimination of male seed may be performed using any known method. The easiest way may be to sort by size or density whenever there is a significant difference of size or other aspect and this may allow one to eliminate small seed or shriveled seeds.

Thus, in a preferred embodiment, after harvesting, a selection of the seeds on their size or density to select the biggest seed on their size or denser seed on their density is performed. This allows improvement of the proportion of hybrid seeds in the seed harvested compared to the seed set in the crop.

According to a feature, limiting self-fertilized male seeds comprises also using a phenotypic marker associated with the male set of plants and/or with the female set of plants, and this marker is used, respectively, either separately or with size or other aspect to discard or to retain seed issuing from self-fertilization of the male set of plants from the hybrids seeds produced on the set of male sterile plants.

A phenotypic marker is preferably associated to the male sterile set of plants, and this marker is used to further discard seed issuing from self-fertilized pollinated male set of plants from the hybrids seeds.

According to a particular feature of the invention, crossing is made with a male plant being a hybrid plant selected for better cross fertilization capacity.

The certification of hybrid seeds requires that at least a given percentage of the harvested seeds comes from cross-fertilization and not from self-fertilization. Thus the hybridity limit of hybrid commercialization for the European certification is currently of 90% for wheat, barley, rape, triticale and rice. If we assume that, in a classical mixed standing production system self-fertilization of the male is twice as frequent as the cross pollination of the female, the male seeds should not exceed some 5% of the total parental seeds sown for the harvested seeds to remain above the 90% hybridity threshold. This proportion of sown male seeds with respect to female seeds may increase owing the elimination of the male plants after anthesis and before harvesting and the possible elimination of seed issuing from self-fertilized pollinated of the male set of plants. The present process is versatile and allows one to obtain a harvest with a wished percentage of undesirable male seed, and this value may be for example of about 15, 10, 5, 4, 3, 2 or 1% with respect to the total harvested seeds after treatment of harvested seeds according to the invention.

The method of the invention offers the main advantage to optimize the ratio of male/female plants sown for this hybrid production in a particular combination of male and female inbred lines in a particular crop, in a particular region or more generally with an expected consequence on fertilization and hybrid seed production and yield. The method allows to have a better seed set because of the close proximity between male and female and good pollen dispersal due to a more favourable ratio between male and female plants. The pollen density on any crop should be improved with a positive effect on the prevention of adventitious pollination from foreign pollen and a consequence on the purity of the harvested seed stock. Another benefit should be to get an easier sowing protocol, since sowing a mix of male and female seeds is rendered possible and this is easier and most cost-effective than drilling strips. Another advantage is that produced hybrids will yield more because they contain more hybrid seeds which perform more than the males.

Cereal lines used for the method of the invention may advantageously be dwarf, semi-dwarf or double-dwarf plants or otherwise and under whatever genetic control of reduced or enhanced stature.

The height difference between the two sets of plants allows an optimization of the pollen diffusion from taller plants to the shorter set of plants, female can be shorter; however standard female and taller male plants may be used as well, as may be shorter males and even shorter females or any other combination that creates a high difference and a desirable hybrid issue. Moreover the sowing as a mix prevent loading of taller male plants.

Generally speaking, the height difference should comply with the technical exigencies of the application itself and can be estimated as being potentially comprised between 1 meter and 10 or 20 centimetres or even less. The more uniform the height of the plants or a crop is, the smaller the required height difference may be. This is why a height different of 5 to 20 cm or even less should also be compliant with the invention. On the other hand, it is may be disadvantageous to have created a big height difference, and to use overly tall male plants, because of the risk of lodging. Therefore, the mean difference of height may ranges from about 5 cm to about 1 m, in particular from about 10 cm to about 60 cm, preferably from about 20 cm to about 50 cm.

The creation and use of a height difference between male and female can be obtained by many different ways which are known from the person skilled in the art. Many dwarf and semi-dwarf genes are known in wheat, for example:

Rht1 now named Rht-B1b (4BS), and Rht2 now named RHT-D1b (4DS) from the Japanese "Norin 10" variety, Rht1 Pearce Stephen (2011), Molecular Characterization of Rht-1 Dwarfing Genes in Hexaploid Wheat. Plant Physiol, Vol 157, p 1820-1831.

Rht1s (Rht-B1d), from Saitama 27 Worland A J and Petrovic S (1988), The gibberellic acid insensitive dwarfing gene from the variety Saitama 27. Euphytica 38:55-63. (allelic to Rht1).

Rht3 named Rht-B1c (4BS—allelic to Rht-B1b) from Tom Thumb, (see Kleijer et al. (1984), Euphytica 33 107-112).

Rht8 (2DS) from the variety "Akakomugi", Gasperini et al. (2012), Genetic and physiological analysis of Rht8 in bread wheat an alternative source of semi-dwarfism with a reduced sensitivity to brassinosteroids. Journal of Experimental Botany. Vol 63 N° 12 p 4419-4436.

Rht9 (7BS), from the variety "Akakomugi", Ellis M. H. et al., (2005) Molecular mapping of gibberellin-responsive dwarfing genes in bread wheat. Theoretical and Applied Genetics, 111:423-430.

Rht10 named Rht-D1c (4DS), from the variety "Taigu" Izumi N et al., Genetic analysis of dwarfness in *Triticum aestivumm* L. Ai_Bian 1, 31, 38-48 (1983).

And others RHT4 (2BL), RHT5, RHT7 (2A), RHT12 (5AL), RHT13 (7BS), RHT14, Rht12.

But dwarf plants can also be obtained by simple selection by choosing short plants in plant breeding populations or from a pyramiding of height QTL (Quantitative Trait Loci), or GMO (Genetically Modified Organism) strategies.

In barley, many mutations affected in plant height are also known, see Franckowiak et al., (1987), Coordinator's report on the semi-dwarf barley collection, Barley Genet News 17:114-115. The most frequently used dwarfism genes are:

Ari-e GP; Uzu, Sdw1, Sdw3 (2HS) Gottwald et al., (2004) The gibberellic-acid insensitive dwarfing gene sdw3 of barley is located on chromosome 2HS in a region that shows high colinearity with rice chromosome 7L, Mol Gen Genomics N° 4, 271: 426-436, Dwarf barley plants can also be obtained by simple selection by choosing short plants in plant breeding populations or from a pyramiding of height QTL (Quantitative Trait Loci), or GMO (Genetically Modified Organism) strategies.

Lines used for this protocol may be short or tall or dwarf or semi dwarf or double dwarf plants howsoever produced and under any mode of genetic control. The invention may start with the creation of a sterile short line.

Basically, the process requires a female (male sterile) plant. Several processes to produce such plants have been described and are known from the person skilled in the art.

Some schemes of use of Cytoplasmic Male Sterility (CMS) in wheat are described in Maan and Lucken (1972), Interacting male sterility restoration Systems for hybrid wheat Research, Crop Science Vol 12, Franckowiak et al., (1976), A proposal for Hybrid Wheat Utilizing *Aegilops squarrosa* L. Cytoplasm, Crop Science, Vol. 16, p 725-728. For a review, see Whitford et al., (2013), Hybrid breeding in wheat: technologies to improve hybrid wheat seed production, Journal of experimental Botany, online 31 Oct. 2013.

The use of CMS has been used to create hybrids in barley: Ahokas H. (1998), Barley, Hybrid Cultivar development in: BANGA, S. S.-BANGA, S. K. (eds), Narosa New Delhi, India, p 316-331. This system uses the two CMS cytoplasms known msm1 and msm2. A fertility restoration for both sterility genes Rfm1a (6H) is known. See respectively, Ahoras H. (1979) cytoplasmic male sterility in barley. III maintenance of sterility and restoration of fertility in the msm1 cytoplasm, Euphytica 28, 409-419; Ahoras H. (1982), Cytoplasmic male sterility in barley XI the msm2 cytoplasm, Genetics 102:285-295; Matsui K. (2001) Molecular mapping of a fertility restoration locus (Rfm1) for cytoplasmic male sterility in barley (*Hordeum vulgare* L.), Theor Appl Genet, 102:477-482.

The production of hybrid cereals may be based on Genetic Male Sterility (GMS) and requires the cross of a male sterile plant homozygous for a recessive gms allele and a male fertile line homozygous for a dominant GMS (i.e. wildtype, normal, fertile) allele at the same gene.

Other ways of producing male sterile plants using GMS systems exist in cereals. Most of these strategies are based on using what is called a maintainer line, which when self-pollinated gives a percentage of female (male sterile) plants used for the hybrid production and a percentage of maintainer plants which may be used for the further production of sterile plants.

Using GMS in wheat may involve:
Recessive ms1 (4BS)
- ms1a from Pugsley variety, Suneson et al., Use of Pugsley's Sterile wheat in Cross breeding, *Crop Science* 2(6): 534-535,
- ms1b from Probus mutant (ionizing radiation mutant), Driscoll C J (1975) Cytogenetic analysis of two chromosomal male-sterility mutants in hexaploid wheat. Australian Journal of Biological Sciences 28:413-416,
- ms1c from Cornerstone (ionizing radiation mutant), Barlow K K and Driscoll C J (1981) Linkage studies involving two chromosomal male-sterility mutants in hexaploid wheat. Genetics 98:791-799,
- ms1d (FS2, EMS mutant), ms1e (FS3), ms1f (FS24) EMS mutants, from Klindworth et al., Chromosomal location of genetic male sterility genes in four mutants of hexaploid wheat, CROP SCIENCE, 2002, 42(5): 1447-1450,
- ms1g from Lanzhou (Zhou K J et al., (2008),) A new male sterile mutant LZ in wheat (*Triticum aestivum* L. Euphytica 159(3): 403-410).

Compensation for ms1 effects on male fertility may involve:
- 5r from *Secale cereal* L. (with a dominant visual marker (hairy pedoncule, hp),
- 2RS, fertility compensation of Cornerstone male sterility of wheat by rye. Hossain M A and Driscoll C J Genetics. 1983 May; 104(1): 181-189,
- 4E, see publication by Zhou K J (2006), The 4E-ms system of producing hybrid wheat. Crop Science 46, 250-255.
  - Dominant Ms2 (4DS) Ta1, Deng and Gao, The use of a dominant male sterile gene in wheat breeding. Acta Agrom Sinica 6: 85-98(1980); Liu B. et al., A dominant gene for male sterility in wheat. Plant Breed 97: 204-209 (1986). Dominant Ms3 (5AS) (male sterility EMS mutant KS87UP9) Maan S S et al., chromosome arm location and gene centromere distance of a dominant gene for male sterility in wheat. Crop Sci. 27 494-500 (1987);
  - Dominant Ms4 (4DS), third dominant male sterility gene in common wheat, Maan S S, Kianian S F, Wheat Information Service, 93: 27-31;
  - Recessive ms5 (3AL) (FS20, EMS mutant) from Klindworth et al., Chromosomal location of genetic male sterility genes in four mutants of hexaploid wheat, CROP SCIENCE, 2002, 42(5): 1447-1450.

Others male sterility systems exists but the sterility is based on external conditions: wptms1 (5B) and wptms2 (5B) from Guo et al., 2006 (Theor Appl Genet 112:1271-1276) and Wptms3 (1BS) from Chen et al., (Biomed & Biotechnol) are thermo photoperiod-sensitive.

Many genic, or genetic, male sterility genes msg has been identified in barley, see Ahokas H. (1998) Barley, Hybrid Cultivar development in: BANGA, S. S.-BANGA, S. K. (eds), Narosa New Delhi, India, p 316-331.

Genetic DNA markers are available for most if not all these mutations, but phenotypic (ie. visible) markers can also be used to follow for example, alleles that compensate for the presence of a gms gene. Some markers associated with the blue pericarp or red colour exist and can be used to facilitate the recovering of sterile or fertile seeds for examples.

a—Use of Chromosome Addition Lines to Compensate for Genic Male Sterility:

This way to create hybrids was the first developed in barley Ramage R. T. (1965, 1991), Balanced tertiary trisomics for use in hybrid seed production, Crop. Sci. 5: 177-178. Chromosome manipulation in barley breeding, Chap 18, Chromosome Engineering in Plants: Genetics, Breeding, Evolution, published par P. K. Gupta, T. Tsuchiya, p 385-400.

In wheat the first example of the use of addition lines is described in the XYZ system of Discroll (1972, 1985, 1986), XYZ system of producing hybrid wheat, Crop Sci. 12: 516-517 (1972), Modified XYZ system of producing hybrid wheat; Crop Science Vol. 25 p 1115-1116 (1985), Nuclear male sterility systems in seed production of hybrid varieties, CRC Critical Reviews in Plant Sciences, Vol. 3, Issue 3 p 227-256, and Driscoll (1986). This system is based on the use of a homologous recessive mutation for male sterility and the use of a "restorer" line containing an additional chromosome carrying a "restorer" gene in one or two copies according to the version of the XYZ system.

The compensating chromosome may also contain a phenotypic marker, e.g. the hairy neck marker of the chromosome 5R from *Secale cereal* L. Discroll (1972), Hossain and Discroll (1983), Fertility compensation of Cornerstone male sterility of wheat by rye Genetics 104:181-189. Other origins of fertility restorer have been tested in Driscoll (1985). The alpha-arm isochromosome of *Triticum urartu*, Jakubz, Chromosome 4 or the long arm isochromosome of a modified barley chromosome 4HmL.

A phenotypic colour genetic marker can be added the previous described system to follow the compensating gene in the progeny; the marker can allow the separating of seed in the progeny as described in WO 92/01366. The phenotypic colour marker can be blue aleurone from chromosome 4 of *Agropyron elongatum* (4 g) see Zeller et al., (1991). Theor Appl Genet. 81(4):551-8, and Zeven A. C., (1991). Wheats with purple and blue grains: a review, Euphytica 56: 243-258. This blue marker is translocated onto the 4-dominant allele-chromosome from *Triticum thaoudar*, *Triticum monococcum* or *Triticum urartu*. This translocated chromosome is further used as an additional chromosome in the XYZ system.

The 4E/MS system described in Zhou K J et al. (2006), The 4E-ms system of producing hybrid wheat. Crop Science 46, 250-255, uses an addition line: 4E (*Agropyron elongatum*) carrying the blue aleurone colour from the gene Ba from *Agropyron* spp. (Bolton E F (1968) Inheritance of blue aleurone and purple pericarp in hexaploid wheat. PhD diss. Colorado Stat Univ. Fort Colins Colo.) with a "gene dosage effect" and the dominant wildtype analogue, MS1, which compensates for the presence of the male sterility allele ms1.

A similar system has been developed by Huang S. S. et al. (1991). The development of a blue marked nucleus male sterile line and its maintainer in bread wheat, Acta Agronomica Sinica. 17:81-87.

The phenotypic marker associated with sterility may also be linked to plant size gene such as a rht mutation. For example the blue seed marker can be added to a chromosome containing the dominant Ms2 gene for male sterility and Rht-D1c (dwarfism). Tian and Liu (2001). Development of dominant nuclear male-sterile lines with a blue seed marker in durum and common wheat, Plant Breeding 120, 79-81. The potential use of this additional line is discussed in Zong-Jun Pu et al. (2005). Studies on breeding of dominant nuclear dwarf male sterile lines with a blue seed marker in common wheat, Wheat Information Services Number 99: 46-50.

b—Use of Addition Substitution Line.

Another way to obtain hybrid cereals is described in WO 92/01366. The restorer line homogenous for 4B containing the recessive mutation for sterility and the additional translocated 4 chromosome, containing the blue coloured marker and the restorer gene, is self-pollinated to obtain a substitution line 2n heterologous for 4B, containing a chromosome carrying the recessive mutation and no colour marker, and the chromosome containing the translocation.

A derived protocol is described by King et al., (1991). Induction of a mutation in the male fertility gene of the preferentially transmitted *Aegilops sharonensis* chromosome 4S and its application for hybrid wheat production, Euphytica 54: 33-39.

In WO 93/13649, another fertility restorer line is described issuing from the previous line following crossing-over between the two 4S chromosomes. This translocation should be obtained with the use of a wheat mutant with altered pairing of homologous chromosomes, for example: (ph1 or ph2), Sutton T. (2003). The Plant Journal 36, 443-456 Able J. (2006). Trends in Plant Science, Vol. 11 N° 6, and Choon-Lin Tiang et al. (2012). Plant Physiol, Vol. 158, p 26-34.

Other different ways to create wheat hybrids are described in WO 03/057848.

Some GMO strategies to create male sterile or female plants are described for example in WO 2005/005641 (See also Whitford et al. et al., (2013) Hybrid breeding in wheat: technologies to improve hybrid wheat seed production, Journal of Experimental Botany, advances Access published October 31).

This invention can also be implemented with a male plant being more vigorous, so that the hybrid may get a better pollination. The hybrid male must be a complete restorer of the sterile female. For example, if the female sterility is based on homozygous recessive ms (as in the 4E-ms) the male needs to be homozygous wild-type.

As explained before, male plants may be still present at the time of harvest and harvested seed stock may still contain self-fertilized male seeds. Phenotypic markers or seed processing can be used to help the removal of those undesirable seeds after harvest and to increase the level of the hybrid seeds in the commercial product.

For example, one may use a seed cleaning equipment, seed sieving, a seed sorter, a gravity table, aspiration, an alveolar sorter, an optical seed sorter. For example, one may use parental lines with an appreciable difference in TGW (Thousand Grain Weight) and the selection can be done on a "Petkus" separator device (U.S. Pat. No. 8,502,019).

Another example is the use of red/white grain colour genes (Sherman J. D. et al. (2008): Microsatellite markers for kernel colour genes in wheat. Crop Science, 48: 1419-1424): The red colour of wheat seeds is controlled by dominant alleles at one or more of three genes: namely R-A1b (on chromosome 3AL), R-B1b (on 3BL) and R-D1b (on 3DL) (Sherman et al., 2008). There is a "dosage effect" of these red-alleles: the more red-alleles carried by a seed are, the more intense is the red colour. The white colour can be obtained in the absence of the red alleles at the 3 locus (r-a1b, r-b1b and r-d1b).

The red-colour is expressed maternally with colouration of the diploid pericarp tissues. It means that whatever the cross, the F1 seeds will be of the same colour as the female parent. Depending on the seed colour, and grain hardness, the wheat grain produced and the ensuing flour milled from it may be directed into different market classes: red and white grained wheat are preferred by particular markets.

It is thus possible to sort if not all, the majority of the male seeds out of a hybrid seed lot by using a seed colour difference between the male seeds and hybrid seeds, for example:

- with a white seeded male line (homozygous r-a1b, r-b1b and r-d1b) and a red seeded female line (homozygous R-A1b, r-b1b and r-d1b/r-a1b, R-B1b and r-d1b/r-a1b, r-b1b and R-D1b/R-A1b, R-B1b and r-d1b/R-A1b, r-b1b and R-D1b/r-a1b, R-B1b and R-D1b OR R-A1b, R-B1b and R-D1b), the hybrid seeds will be red and male seeds from self-pollination will be white.
- with a red seeded male line (homozygous R-A1b, r-b1b and r-d1b/r-a1b, R-B1b and r-d1b/r-a1b, r-b1b and R-D1b/R-A1b, R-B1b and r-d1b/R-A1b, r-b1b and R-D1b/r-a1b, R-B1b and R-D1b OR R-A1b, R-B1b and R-D1b) and a white seeded female line (homozygous r-a1b, r-b1b and r-d1b), the hybrid seeds will be white and male seeds from self-pollination will be red.
- with a light red seeded male line (homozygous R-A1b, r-b1b and r-d1b/r-a1b, R-B1b and r-d1b/r-a1b, r-b1b and R-D1b) and with a dark red seeded female line (homozygous R-A1b, R-B1b and R-D1b), the hybrid seeds will be dark red and the self-pollinated male seeds will be light red.
- with a dark red seeded male line (homozygous R-A1b, R-B1b and R-D1b) and a light red seeded female line (homozygous R-A1b, r-b1b and r-d1b/r-a1b, R-B1b and r-d1b/r-a1b, r-b1b and R-D1b), the hybrid seeds will be light red and the self-pollinated male seeds will be dark red.

The next generation (F2) seeds of the first hybrid will be red in any situation as the hybrid plants would be homozygous for one of the three red genes.

The seed sorting can be achieved using any conventional optical sorting machine able to separate white seeds from red seeds or light red seeds from dark red seeds. Sorting of seed for these colours using of NIR is described in Wang et al., (1999). Single Wheat Kernel Colour Classification by Using Near-Infrared reflectance Spectra Cereal Chemistry, Vol. 76, No 1.

Seeds can be also sorted by their size on a specific sieve (2.8 mm for example) to remove smallest or shrivelled seeds, which are generally of shorter size than the hybrids.

The present invention will now be described using non-limiting examples.

FIG. 1 is a schema of a field experiment.

Example 1: Wheat

To create the desired height difference, the dwarf genes available in wheat were used. A double dwarf female Rht-B1b/Rht-B1b, Rht-D1b/Rht-D1b (alleles with additive effects) in combination with a wild-type male Rht-B1a/Rht-B1a, Rht-D1a/Rht-D1a were used. Preferably, the wild-type male is not susceptible to lodging. Preferably, the Rht-B1b/Rht-B1a, Rht-D1b/Rht-D1a hybrid is chosen to have an intermediate height, close to that of a commercial line (mostly either Rht-B1b/Rht-B1b, Rht-D1a/Rht-D1a or Rht-B1a/Rht-B1a, Rht-D1b/Rht-D1b).

Determination of the Seed Stock Reduction by Glyphosate Application at Post-Anthesis:

Field Test on Different Genotypes

At post-anthesis, plants of 5 European winter wheat elite lines were treated by hand-applying to the spikes a brush soaked with a solution of glyphosate at 120 g/l (recommended for weed wiping in UK). At full maturity, spikes of treated and untreated plants from the main stem as well as from tillers were harvested and their fertility was determined and expressed as the ratio number of seeds/spikelet. 7 to 12 repetitions from untreated plants and 20 to 24 repetitions from treated plants were harvested for each of the 5 elite lines.

TABLE 1

Results of field tests

| | | Seeds/Spikelet | | | % non germinating seeds | |
|---|---|---|---|---|---|---|
| | | Average value | standard deviation | repetitions | Total seeds tested | % |
| Alixan | UNTREATED | 2.14 | 0.6 | 12 | 60 | 8.3% |
| Alixan | TREATED | 2.36 | 0.5 | 22 | 120 | 90.0% |
| Allezy | UNTREATED | 1.70 | 0.5 | 7 | 60 | 5.0% |
| Allezy | TREATED | 2.12 | 0.5 | 24 | 120 | 68.3% |
| Altigo | UNTREATED | 1.94 | 0.4 | 10 | 60 | 31.7% |
| Altigo | TREATED | 2.02 | 0.4 | 22 | 120 | 69.2% |
| Buster | UNTREATED | 2.09 | 0.9 | 10 | 60 | 16.7% |

TABLE 1-continued

Results of field tests

| | | Seeds/Spikelet | | | % non germinating seeds | |
|---|---|---|---|---|---|---|
| | | Average value | standard deviation | repetitions | Total seeds tested | % |
| Buster | TREATED | 2.12 | 0.7 | 22 | 120 | 78.3% |
| Charger | UNTREATED | 1.79 | 0.9 | 8 | 60 | 13.3% |
| Charger | TREATED | 2.04 | 0.7 | 20 | 120 | 85.0% |
| MEAN | UNTREATED | 1.93 | 0.66 | 9 | 60 | 15.0% |
| MEAN | TREATED | 2.13 | 0.58 | 22 | 120 | 78.2% |

As can be concluded from the above table, the average number of seeds by spikelets (average value) from untreated plants was 1.93 (standard deviation of 0.66) and the fertility of spikes from treated plants was 2.13 (standard deviation of 0.58). The seed set of untreated and treated plants were not statistically different. This herbicide treatment experiment did not significantly reduce the number of seed per spike harvested.

However, the seeds of treated spikes were shriveled in comparison to the seeds of untreated spikes. These shriveled seeds were of smaller size and relatively easy to remove during post-harvest seed processing. Shriveled seed is unlikely to develop into a normal plant. On average 78.2% of the seeds from treated spikes (120 seeds tested per line) were unviable (do not germinate) compared to 15.0% of seeds from untreated spikes (60 seeds tested per line).

Glasshouse Test of Herbicide Application Timing

An experiment was conducted in our greenhouse by applying a solution of glyphosate at 120 g/l to the main spike of plants of the cultivar Apache with a soaked anti-drop brush at the 4 following development stages:

Main spike at anthesis (treatment 1),

Main spike at post-anthesis, no secondary tiller yet at anthesis (treatment 2),

Main spike at post-anthesis, secondary tiller(s) at anthesis (treatment 3),

Main spike at post-anthesis, secondary tiller(s) at post-anthesis (treatment 4), At least 10 spikes per treatment were treated with glyphosate. Main spikes (further named "spikes from main stem") as well as spikes from tillers (further named "spikes from secondary stems") were harvested and threshed to determine the seedset/spike.

TABLE 2

Results of glasshouse test

| | SPIKES MAIN STEM | | | | SPIKES SECUNDARY STEMS | | | |
|---|---|---|---|---|---|---|---|---|
| | | SEEDSET | | | | SEEDSET | | |
| Treatments | number | MEAN | STDDEV | shrivelled | number | MEAN | STDDEV | shrivelled |
| untreated | 19 | 34.2 | 10.7 | 2.9% | 28 | 25.9 | 9.1 | 5.8% |
| 1 | 19 | 0 | | | 20 | 10.8 | 17.2 | 0% |
| 2 | 18 | 6.7 | 11.9 | 60.0% | 22 | 14.2 | 18.6 | 10.5% |
| 3 | 15 | 30.3 | 6.4 | 100.0% | 25 | 22.8 | 15.3 | 42.3% |
| 4 | 14 | 38.1 | 6.8 | 67.4% | 18 | 34.7 | 13.7 | 11.8% |

As can be observed from the above table 2, for the untreated spikes (control), the average seed set/spike on 19 spikes was of 34.2 on main stems and of 25.9 on 28 spikes on secondary stems.

For the spikes treated with treatment 1, no seeds were produced on the spikes of the main stems and the seed set on spikes of secondary stems was largely reduced compared to the untreated treatment control (on average 10.8 against 25.9).

For the spikes treated with treatment 2 i.e. treated just at post-anthesis, the spikes of the main stems produced on average only 19.6% of the seed set produced by untreated spikes. The majority of those seeds were shriveled (60%). The spikes on the secondary tillers were far from yielding normal seed sets (14.2).

For the spikes treated with treatment 3, seed sets of the treated main spikes showed a close to normal fertility, but yielding only shriveled seeds. The spikes on secondary tillers showed a relatively normal fertility, but 42.3% of the seeds produced were shriveled.

For the spikes treated with treatment 4, the glyphosate treatment made after anthesis at the plant level did not impede fecundity, but on the treated main spike the majority of the seeds are shriveled (67.4%). The high seed set on untreated tillers might be an effect of nutriment redistribution inside the plant.

The conclusion of this experiment is that every spike treated at post-anthesis was able to set seeds, but that the majority (67.4%) of those seeds were shriveled and would have been eliminated during seed processing. The diffusion of glyphosate inside the plant appeared to affect the fertility of an untreated spike on the same plant unless the untreated spikes had reached anthesis. As the treatment with glyphosate will be only implemented when the whole plant will have terminated flowering, every spike not directly reached by the treatment should be able to produce a majority of viable seeds but these seed are mainly shriveled. Even if not offering a complete elimination of the male seeds, a post-anthesis treatment with glyphosate will significantly reduce the male seed stock, enabling improving the ratio female/male in the mix-standing production system.

The ability to produce viable plantlets will be tested on subset of seeds of the treatments "untreated" and "traitement 4".

The same experiment has been repeated on the elite line Alixan.

Field Test in a Simulated Mixed Stand Production

A simulation test for hybrid production was implemented. A short commercial variety (Courtot, homozygous Rht-B1b-Rht-D1b) a fertile dwarf line, simulates the «female» and a wildtype tall commercial variety (Alhambra, homozygous Rht-B1a-Rht-D1a) a fertile mid-tall line, simulates the «male». These two lines have a similar earliness and were mixed at sowing with the following rates:

95% Courtot mixed with 5% Alhambra,
90% Courtot mixed with 10% Alhambra,
85% Courtot mixed with 15% Alhambra,
80% Courtot mixed with 20% Alhambra, Two controls, with respectively, 100% Courtot and 100% Alhambra were included.

FIG. 1 is a schema of the field experiment, each box represents a block or plot of 1.5 m×6 m, with description of the species sowed: Courtot (sowing of Courtot seed only), Alhambra (sowing of Alhambra seeds only), Courtot-AL-95/5 (sowing of a mix of 95% of Courtot and 5% of Alhambra), Courtot-AL-90/10 (sowing of a mix of 90% of Courtot and 10% of Alhambra), Courtot-AL-85/15 (sowing of a mix of 85% of Courtot and 15% of Alhambra), Courtot-AL-80/20 (sowing of a mix of 80% of Courtot and 20% of Alhambra).

Legends: situation on the field is given by crossing the numbers of plots on the left on FIG. 1 and the number at the bottom of FIG. 1:

Plots situated at 13-18/2, 13-18/5, 7-12/3 and 1-6/4: no treatment
Plots situated at 13-18/3, 7-12/4, 1-6/2 and 1-6/5: 1 treatment
Plots situated at 13-18/4, 7-12/2, 7-12/5 (plots not considered in the results) and 1-6/3: 2 treatments.

At harvest, the seedset on the female is considered as the virtual hybrid seeds. The experiment is consequently a bit biased as this virtual hybrid seedset is rather optimal. Glyphosate at 120 g/l is applied at post-anthesis on the «male» plants with a soaked sponge with one way application (1 treatment) or a two way (opposite) application (2 treatments). Four repetitions were done for each condition according the field experiment described in FIG. 1.

Results are in table 3: On the plots with Alhambra alone, we observed a moderate to strong lodging explaining the reduced yield. By contract no lodging of Alhambra was observed in the Courtot-Alhambra plots: Courtot is acting as a support. The lodging susceptibility of the male could be consequently significantly reduced in a mix-standing production system. The treatment on the Alhambra spikes, which consequence is the reduction of their seedsets, limited the yield in the mixed plots up to 51.8% (Mix Courtot-AL-80/20, 2 treatments). This result indicates—that the percentage of male plants in the hybrid production has to be restricted to limit the impact on the female yield.

TABLE 3 yield results for plots sowed with Courtot or Alhambra alone or mix of courtot and Alhambra seeds. Results in tons/ha. The reduction % is the reduction of yield for a combination of Courtot and Alhambra sowing with one or two treatment(s) related to the same condition without treatment.

| | YIELD in tons | | | | |
|---|---|---|---|---|---|
| | 0 treatment | 1 treatment | | 2 treatments | |
| | ton/ha | ton/ha | Reduction % | ton/ha | Reduction % |
| Alhambra | 3.63 | 5.98 | | 5.60 | |
| Courtot | 5.88 | 5.26 | | 5.66 | |
| Courtot-AL-80/20 | 5.53 | 3.44 | 37.7% | 2.67 | 51.8% |
| Courtot-AL-85/15 | 5.19 | 3.17 | 38.8% | 3.17 | 38.8% |
| Courtot-AL-90/10 | 5.76 | 3.95 | 31.4% | 3.67 | 36.3% |
| Courtot-AL-95/5 | 5.37 | 4.41 | 17.8% | 4.28 | 20.1% |

Molecular markers on the Rht-B1b and Rht-D1b genes were used to identify Courtot seeds (representing hybrid seed in our model) and Alhambra seeds representing male seeds in our model. 24 seeds from every individual plot were analyzed and the results are showed in table 4.

Due to the concurrence of the tall male plant over the short female plants, the male seed quantity over the female seed quantity is roughly doubled at harvest versus the quantity at sowing in the condition without treatment. For instance, in the mix "Courtot-Alhambra-90%/10%", Alhambra made 10% of the seeds at sowing but their proportion rose to 19.7% at harvest. Without a male partial destruction or elimination, a mix-standing production with a tall male would not be viable. A double/both ways application seems more efficient than a single application. For instance, in the mix "Courtot-Alhambra-90%/10%" and with a two-ways treatment, the proportion of Alhambra seeds at harvest was reduced to 2.2% which translates into a hybridity of 97.8%. With a double/both ways application the «hybridity» of the harvested lots is always above 90%.

TABLE 4 for every seed mix and every treatment, the percentage of "male" seeds (Alhambra) is indicated at sowing and at harvest. The virtual hybridity is calculated as the percentage of "female seeds" (Courtot) into the harvested lot. Treatment 0 corresponds to plots with no treatment, treatment 1 to plots with a glyphosate treatment in one application and treatment 2 to glyphosate treatment with a two way applications. "Sowing" correspond to the percentage of Alhambra seed in the mixed sowing and "harvest" the percentage of Alhambra seeds in the seeds harvested.

| | | % ALHAMBRA | | Virtual |
|---|---|---|---|---|
| | Treatment | SOWING | HARVEST | hybridity % |
| Courtot-Alhambra-80%/20% | 0 | 20 | 35.8 | 64.2 |
| | 1 | 20 | 24.1 | 75.9 |
| | 2 | 20 | 5.1 | 94.9 |
| Courtot-Alhambra-85%/15% | 0 | 15 | 37.5 | 62.5 |
| | 1 | 15 | 10.1 | 89.9 |
| | 2 | 15 | 2.4 | 97.6 |
| Courtot-Alhambra-90%/10% | 0 | 10 | 19.7 | 80.3 |
| | 1 | 10 | 10.8 | 89.2 |
| | 2 | 10 | 2.2 | 97.8 |

TABLE 4-continued for every seed mix and every treatment, the percentage of "male" seeds (Alhambra) is indicated at sowing and at harvest. The virtual hybridity is calculated as the percentage of "female seeds" (Courtot) into the harvested lot. Treatment 0 corresponds to plots with no treatment, treatment 1 to plots with a glyphosate treatment in one application and treatment 2 to glyphosate treatment with a two way applications. "Sowing" correspond to the percentage of Alhambra seed in the mixed sowing and "harvest" the percentage of Alhambra seeds in the seeds harvested.

| | | % ALHAMBRA | | Virtual |
|---|---|---|---|---|
| | Treatment | SOWING | HARVEST | hybridity % |
| Courtot-Alhambra-95%/5% | 0 | 5 | 11.6 | 88.4 |
| | 1 | 5 | 3.4 | 96.6 |
| | 2 | 5 | 0.0 | 100 |
| Alhambra | 0 | 100 | 100.0 | |
| | 1 | 100 | 98.9 | |
| | 2 | 100 | 96.7 | |
| Courtot | 0 | 0 | 0.0 | 100 |
| | 1 | 0 | 0.0 | 100 |
| | 2 | 0 | 0.0 | 100 |

Example 2: Barley

Preliminary tests of herbicide application were done in summer 2013, when glyphosate was applied, at the rate recommended by the provider, to tall barley plants in plots of shorter barley using a weed wiper. It was observed that tall barley can be destroyed without damaging semi dwarf barley plants present on the same plots.

The same experiment was done with a cutting tool on a mix of tall and shorter plants and the tall plants can be selectively cut.

An hybrid production was also made between two barley lines, designated genotypes A and B. The harvested seed set was dressed using a seed grading device. Three different seed grades were produced with large seed sizes: superior to 2.8 mm, medium i.e. superior to 2.5 mm and small i.e. inferior to 2.5 mm. A molecular analysis of these seed batches showed that hybrid seeds are mainly in the first batch, with a larger seed size. The proportion of hybrids seeds which haven't been graded was 72% while the proportion of hybrids seeds in the superior 2.8 mm sub-sample was 96%.

This experiment showed that the use of a seed sorting device can increase the proportion of hybrid seeds in harvested seed lots.

The invention claimed is:

1. A method of producing hybrid cereal seeds comprising:
(a) mix-sowing parental seeds consisting of a mixture of a first set of parental seeds for shorter female (male sterile) plants and a second set of parental seeds for taller male fertile plants, wherein:
  (i) the second set of parental seeds for taller male fertile plants comprises 15% or less of the total number of parental seeds at mix-sowing, and
  (ii) the shorter female (male sterile) plants are dwarf, semi-dwarf or double-dwarf plants and the male fertile plants are taller than the female (male sterile) plants at anthesis,
(b) allowing crossing said shorter female (male sterile) plants with said taller male fertile plants,
(c) passing a tool extending at a height that is above the height of the shorter female plants between anthesis and up to 10 days after anthesis of the male fertile plants comprising main stems or main and secondary stems, wherein said tool is motor driven or supported by a motor driven vehicle and is moved in order to contact the male fertile plants and not the female plants that are shorter and below the height of the tool, and said tool applies by this contact an herbicide on said taller male fertile plants standing above this height in order to prevent or reduce normal self-fertilized male seeds development, and to produce no or residual shriveled self-fertilized male seeds on the main stems and/or on the secondary stems,
(d) harvesting the seeds and obtaining harvested seeds comprising hybrid seeds and male seeds, said male seeds representing from 1 to 15% of said harvested seeds, wherein said harvested male seed comprise a portion of shriveled self-fertilized male seeds, and
(e) sorting the harvested seeds by size using a sieve to remove undesirable shriveled self-fertilized male seeds that are shorter in size than said hybrid seeds, and recovering hybrid cereal seeds with a limited amount of self-fertilized male seeds,
wherein the cereal is selected from the group consisting of oat, wheat, barley, rice, spelt, triticale, millet, and rye.

2. The method of claim 1, wherein the herbicide used is systemic.

3. The method of claim 1, wherein the second set of parental seeds for taller male fertile plants comprises 5% to 15% of the total number of parental seeds at mix-sowing.

4. The method of claim 1, wherein the height mean difference between female (male sterile) plants and male fertile plants ranges from about 5 cm to about 1 m.

5. The method of claim 1, wherein limiting the self-fertilized male seed proportion comprises further, after harvesting, a further selection of the seeds to remove undesirable self-fertilized male seeds, using a phenotypic character.

6. The method of claim 5, wherein a phenotypic marker is associated with the female (male sterile) and/or male fertile set of plants, and this marker is used to further discard seeds issuing from self-fertilized male plants from the hybrid seeds.

7. The method of claim 1, wherein limiting the self-fertilized male seed proportion is performed in order to obtain at least 90% of hybrid seeds of the total seeds produced.

8. The method of claim 1, wherein the tool is a weed wiper.

9. The method of claim 1, wherein the herbicide comprises glyphosate.

10. The method of claim 4, wherein the height mean difference between female (male sterile) plants and male fertile plants ranges from about 10 cm to about 60 cm.

11. The method of claim 4, wherein the height mean difference between female (male sterile) plants and male fertile plants ranges from about 20 cm to about 50 cm.

12. The method of claim 1, wherein the tool comprises a horizontal bar that is moveable, being motor driven or supported by a motor driven vehicle.

13. The method of claim 12, wherein the height at which the bar is placed is adjustable.

14. The method of claim 13, wherein the bar height may be altered while travelling through a crop.

15. The method of claim 1, wherein the seeds harvest comprises at least 89.2% of hybrid seeds with respect to the total seeds in the harvest.

16. The method of claim 1, wherein the seeds harvest comprises at least 89.9% of hybrid seeds with respect to the total seeds in the harvest.

17. The method of claim 1, wherein the seeds harvest comprises at least 96.6% of hybrid seeds with respect to the total seeds in the harvest.

18. The method of claim 1, wherein the herbicide is applied twice on the male fertile plants.

19. A method of producing hybrid cereal seeds comprising:
- (a) mix-sowing of parental seeds consisting of a mixture of a first set of parental seeds for shorter female (male sterile) plants and a second set of parental seeds for taller male fertile plants, wherein:
  - (i) the second set of parental seeds for taller male fertile plants represents 15% or less of the total number of parental seeds at sowing, and
  - (ii) the shorter female (male sterile) plants are dwarf, semi-dwarf or double-dwarf plants and the male fertile plants are taller than the female (male sterile) plants at anthesis,
- (b) allowing crossing the shorter female (male sterile) plants with said taller male fertile plants,
- (c) passing a tool extending at a height that is above the height of the shorter female plants between anthesis and up to 10 days after anthesis of the male fertile plants comprising main stems or main and secondary stems wherein said tool is motor driven or supported by a motor driven vehicle and is moved in order to contact the male fertile plants and not the female plants that are shorter and below the height of the tool, and said tool applies by this contact an herbicide on the male fertile plants standing above this height in order to prevent or reduce normal self-fertilized male seeds development, and to produce no or residual shriveled self-fertilized male seeds on the main stems, on the secondary stems, or on both main and secondary stems,
- (d) harvesting the seeds comprising hybrid seeds and male seeds, said male seeds representing from 1 to 15% of the harvested seeds, wherein said harvested male seeds comprise a portion of shriveled self-fertilized male seeds and obtaining a seeds harvest comprising at least 89.2% of hybrid seeds with respect to the total seeds in the harvest, and
- (e) sorting the seeds of the seeds harvest by size using a sieve to remove undesirable shriveled self-fertilized male seeds that are shorter in size than said hybrid seeds, and recovering hybrid cereal seeds with a limited amount of self-fertilized male seeds, wherein the cereal is selected from the group consisting of oat, wheat, barley, rice, spelt, triticale, millet, and rye.

20. The method of claim 19, wherein the second set of parental seeds for taller male fertile plants comprises 5% to 15% of the total number of parental seeds at sowing.

21. The method of claim 19, wherein the seeds harvest comprises at least 89.9% of hybrid seeds with respect to the total seeds in the harvest.

22. The method of claim 19, wherein the seeds harvest comprises at least 96.6% of hybrid seeds with respect to the total seeds in the harvest.

23. The method of claim 19, wherein the herbicide is applied twice on the male fertile plants.

* * * * *